United States Patent
Flynn et al.

(10) Patent No.: US 6,602,866 B2
(45) Date of Patent: Aug. 5, 2003

(54) MERCAPTOACETYLAMIDE DERIVATIVES, A PROCESS FOR THEIR PREPARATION AND THEIR USE

(75) Inventors: Gary A. Flynn, Broomall, PA (US); Barbara A. Anderson, Cincinnati, OH (US); Manfred Gerken, Marburg (DE); Bernd Jablonka, Oberursel (DE); Heinz-Werner Kleemann, Bischofsheim (DE); Wolfgang Linz, Mainz (DE); Werner Seiz, Frankfurt am Main (DE); Bernhard Seuring, Hofheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/118,179

(22) Filed: Apr. 8, 2002

(65) Prior Publication Data

US 2002/0193589 A1 Dec. 19, 2002

Related U.S. Application Data

(60) Provisional application No. 60/283,305, filed on Apr. 12, 2001.

(51) Int. Cl.$^7$ .................. A61K 31/55; C07D 223/14; C07D 487/00; C07D 491/00
(52) U.S. Cl. .................. 514/212.04; 514/212.05; 514/212.06; 540/519; 540/521; 540/522
(58) Field of Search ................. 540/519, 521, 540/522; 514/212.04, 212.05, 212.06

(56) References Cited

U.S. PATENT DOCUMENTS

| | | | |
|---|---|---|---|
| 3,334,091 A | 8/1967 | Houlihan | |
| 3,334,095 A | 8/1967 | Houlihan | |
| 4,080,449 A | 3/1978 | Croisier et al. | |
| 4,320,057 A | 3/1982 | Freed et al. | |
| 4,391,752 A | 7/1983 | Crossley | |
| 4,399,136 A | 8/1983 | Hassall et al. | |
| 4,415,496 A | 11/1983 | Harris et al. | |
| 4,487,929 A | 12/1984 | Hassall et al. | |
| 4,512,924 A | 4/1985 | Attwood et al. | |
| 4,584,294 A | 4/1986 | Ruyle | |
| 4,658,024 A | 4/1987 | Attwood et al. | |
| 4,692,438 A | 9/1987 | Hassall et al. | |
| 4,716,232 A | 12/1987 | Ternansky | |
| 4,734,504 A | 3/1988 | Holmes | |
| 4,734,505 A | 3/1988 | Holmes | |
| 4,762,924 A | 8/1988 | Hassall et al. | |
| 4,772,701 A | 9/1988 | Attwood et al. | |
| 4,782,149 A | 11/1988 | Lawton et al. | |
| 4,785,093 A | 11/1988 | Hassall et al. | |
| 4,808,713 A | 2/1989 | Attwood et al. | |
| 4,824,832 A | 4/1989 | Flynn et al. | |
| 4,826,980 A | 5/1989 | Hassall et al. | |
| 4,973,585 A | 11/1990 | Flynn et al. | |
| 5,208,230 A | 5/1993 | Flynn et al. | |
| 5,238,932 A | 8/1993 | Flynn et al. | |
| 5,366,973 A | 11/1994 | Flynn et al. | |
| 5,424,425 A | 6/1995 | Flynn et al. | |
| 5,430,145 A | * 7/1995 | Flynn et al. | 540/521 |
| 5,488,048 A | 1/1996 | Flynn et al. | |
| 5,491,143 A | 2/1996 | Flynn et al. | |
| 5,527,795 A | 6/1996 | Flynn et al. | |
| 5,529,995 A | 6/1996 | Flynn et al. | |
| 5,679,671 A | * 10/1997 | Oinuma et al. | 514/211 |
| 6,013,645 A | * 1/2000 | Flynn et al. | 514/214 |

FOREIGN PATENT DOCUMENTS

| | | |
|---|---|---|
| EP | 0128728 | 12/1984 |
| EP | 0249223 | 12/1987 |
| EP | 0249224 | 12/1987 |
| EP | 0322914 | 7/1989 |
| EP | 0533084 | 3/1992 |
| EP | 481 522 | * 4/1992 |
| EP | 0481522 | 4/1992 |
| EP | 0492369 | 7/1992 |
| EP | 0534363 | 3/1993 |
| EP | 0534396 | 3/1993 |
| EP | 0599444 | 6/1994 |
| EP | 0657453 | 6/1995 |
| EP | 0671172 | 9/1995 |
| WO | 9108195 | 6/1991 |
| WO | 9109840 | 7/1991 |
| WO | 9302099 | 2/1993 |
| WO | 9316103 | 8/1993 |
| WO | WO 95/21839 | * 8/1995 |

OTHER PUBLICATIONS

De Lombaert et al. Dual Inhibition of Angiotensin–Converting Enzyme and Neutral Endopeptidase By Tricyclic Benzazepinone Thiols Bioorg. Med. Chem. Lett. 6, 2875–2880 (1996).

(List continued on next page.)

*Primary Examiner*—Bruce Kifle
(74) *Attorney, Agent, or Firm*—Lawrence L. Martin; Balaram Gupta

(57) ABSTRACT

This invention discloses and claims a series of mercaptoacetylamide derivatives of formula I. Also disclosed and claimed are pharmaceutical compositions incorporating these compounds and processes for preparing said compounds. The use of said compounds for inhibition of the enzymes angiotensin converting enzyme and neutral endopeptidase, and for the treatment of hypertension and congestive heart failure are also disclosed and claimed

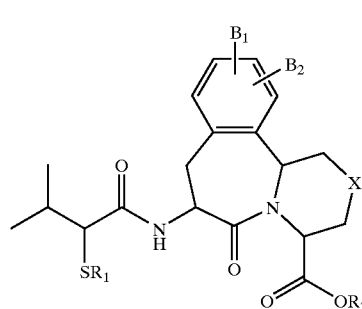

22 Claims, 1 Drawing Sheet

OTHER PUBLICATIONS

Figure 1:
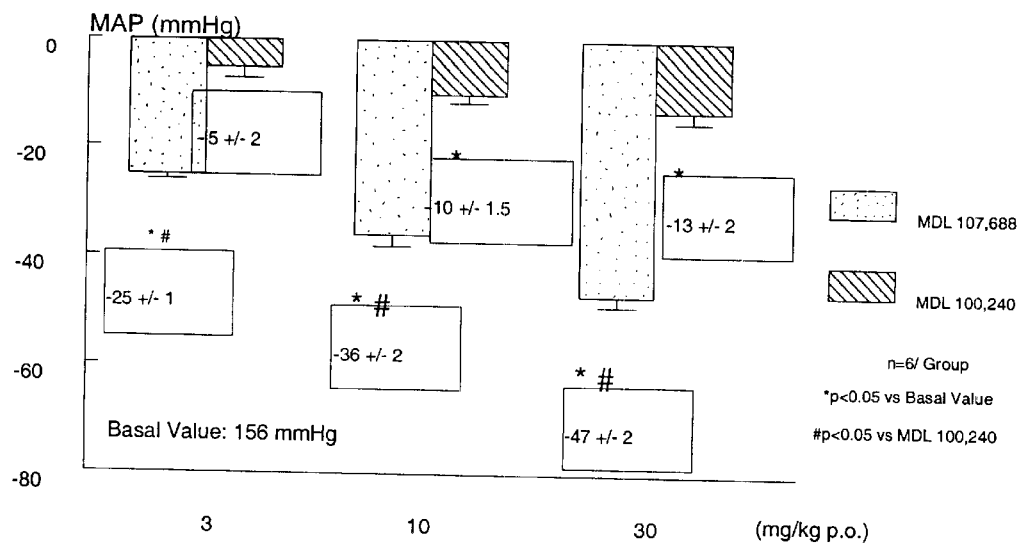

Flynn et al. an Acyl–Iminum Ion Cyclization Route to a Novel Conformationally Restricted Dipeptide Mimic: Applications to Angiotensin–Converting Enzyme Inhibition J. Amer Chem. Soc. 109, 7914–7915 (1987).

Flynn et al. An Acyl–Iminium Ion Cyclization Route to Novel. Conformationally Restricted Dipeptide Mimics: Application to Angiotensin—Converting Enzyme Inhibition Peptide Chemistry 631–636 (1987); T. Shiba and S. Sakakibara (ed.), Protein Research Foundation, Osaka (1988).

Flynn et al. The Conversion of a Diazolactam to an α–Methylenelactam: An Entrance to New Conformationally Restricted Inhibitors of Angiotensin—Converting Enzyme Tetrahedron Letters, 31, 815–818 (1990).

Attwood et al. The Design and Synthesis of the Angiotensin Converting Enzyme Inhibitor Cilazapril and Related Bicyclic Compounds J. Chem. Soc. Perkin Trans. I, 1011–1019 (1986).

I. L. Natoff and S. Redshaw Angiotensin—Converting Enzyme Inhibitors—Cilazapril and Other Bicyclic Hexahydropyridazines Drugs of the Future, 12, 475–483 (1987).

Powell et al. Suppression of the Vascular Response to Injury: The Role of Angiotensin—Converting Enzyme Inhibitors Journal of American College of Cardiology, 17, 137B–142B (1991).

Davis Jr. et al. Atrial Natriuretic Factor and the Neutral Endopeptidase Inhibitor SCH42495 Prevent Myointimal Proliferation after Vascular Injury Circulation, Supplement I, 86, I–220 (abstract 0873) (Oct. 1992).

Ocain et al. New Modified Heterocyclic Phenylalanine Derivatives. Incorporation into Potent Inhibitors of Human Renin J. Med. Chem., 35, 823–832 (1992).

Flynn et al. An Acyliminium Ion Route to cis and trans "Anti" Phe–Gly Dipeptide Mimetics Bioorg. Med. Chem. Lett., 1, 309–312 (1991).

Fournie–Zaluski et al. "Mixed Inhibitor–Prodrug" as a New Approach Toward Systemically Active Inhibitors of Enkephalin—Degrading Enzymes J. Med. Chem., 35, 2473–2481 (1992).

Fournie–Zaluskie et al. Potent and Systemically Active Aminopeptidase N Inhibitors Designed from Active–Site Investigation J. Med. Chem., 35. 1259–1266 (1992).

French et al. Characterization of a Dual Inhibitor of Angiotensin I–Converting Enzyme and Neutral Endopeptidase J. Pharmacol. Exptl. Therap., 268, 180–186 (1994).

Parsons et al. Benzolactams: A New Class of Converting Enzyme Inhibitors Biochem. Biophys. Res. Commun., 117, 108–113 (1983).

Burkholder et al. The Synthesis of 6–Amino–5–oxo–7–phenyl–1,4–oxazepines as Conformationally Constrained Gauche (–) Dipeptide Mimetics Bioorg. Med. Chem. Lett., 3, 231–234 (1993).

Flynn et al. Application of a Conformationally Restricted Phe–Leu Dipeptide Mimetic to the Design of a Combined Inhibitor of Angiotensin I–Converting Enzyme and Neutral Endopeptidase 24.11 J. Med. Chem., 36, 2420–2423 (1993).

Robl et al. Stereoselective Routes Towards the Generation of Novel Bicyclic Azepinones as Conformationally Restricted Dipeptide beta–Turn Mimetics $34^{th}$ National Organic Symposiuim, Poster 133 abstract, Jun. 11–15, 1995.

Oinuma et al. The Creation of Isoleucine Derivatives as Orally–Potent, Dual Inhibitors of NEP and ACE: Design and Pharmacology $209^{th}$ American Chemical Society Meeting, Anaheim CA, Apr. 2–7, 1995, Poster MEDI 161.

Simpkins et al. Dual ACE/NEP Inhibitors: Synthesis and Activity of Mercaptoacyl Dipeptides Containing Conformationally Restricted Dipeptide Surrogates $210^{th}$ American Chemical Society Meeting, Chicago, IL, Aug. 20–24, 1995, Poster MEDI 064.

Brown et al. Improved Procedure for the Asymmetric Reduction of Prochiral Ketones by β–(3–Pinanyl)–9–borabicyclo[3.3.1]nonane J. Org. Chem., 47, 1606–1608 (1982).

Midland et al. Asymmetric Reduction of Prochiral Ketones with β–(3–Pinanyl)–9–borabicyclo[3.3.1]nonane in Efficiencies Approaching 100%. Simultaneous Rate Enhancement and Side Reaction Suppression via the Use of Elevated Pressures. J. Org. Chem., 49, 1316–1317 (1984).

Brown et al. Remarkable Optical Induction in the Reduction of α–Keto Esters with β–(3–Pinanyl)–9–borabicyclo[3.3.1] nonane. Synthesis of α–Hydroxy Esters of 100% Optical Purity J. Am. Chem. Soc., 106, 1531–1533 (1984).

* cited by examiner

Dose-Dependent Blood Pressure Reduction in SHR after oral MDL 107,688 and MDL 100,240 - Telemetric Measurement MDL 100,240 is [4S-[4α,7α(S),12bβ]]-7-[(1-oxo-2(S)-acetylthio-3-phenylpropyl)-amino]-1,2,3,4,6,7,8,12b-octahydro-6-oxo-pyrido[2,1a][2]benzazepine-4-carboxylic acid.

MDL 107,688 is [4S-[4α,7α(S),12bβ]]-7-[[2(S)-acetylthio-3-methyl-1-oxobutyl]amino]-1,2,3,4,6,7,8,12b-octahydro-6-oxo-pyrido[2,1a][2]benzazepine-4-carboxylic acid.

MERCAPTOACETYLAMIDE DERIVATIVES, A PROCESS FOR THEIR PREPARATION AND THEIR USE

This application claims the benefit of U.S. Provisional Application No. 60/283,305, filed Apr. 12, 2001.

BACKGROUND OF THE INVENTION

1. Field of the Invention

The present invention is directed to novel compounds possessing both angiotensin converting enzyme inhibitory activity and neutral endopeptidase inhibitory activity and methods of preparing such compounds. The present invention is also directed to pharmaceutical compositions containing such dual inhibiting compounds or pharmaceutically acceptable salts thereof and their use in the manufacture of medicaments.

2. Description of the Art

Angiotensin-Converting Enzyme (ACE) is a peptidyl dipeptidase which catalyzes the conversion of angiotensin I to angiotensin II. Angiotensin II is a vasoconstrictor which also stimulates aldosterone secretion by the adrenal cortex. ACE inhibition prevents both the conversion of angiotensin I to angiotensin II and the metabolism of bradykinin, resulting in decreased circulating angiotensin II, aldosterone and increased circulating bradykinin concentrations. In addition to these neurohormonal changes, decreases in peripheral resistance and blood pressure are observed, particularly in individuals with high circulating renin. Other pharmacological effects associated with ACE inhibition include regression of left ventricular hypertrophy, improvement in the clinical signs of heart failure, and reduction in mortality in patients with congestive heart failure (CHF) or left ventricular dysfunction after myocardial infarction.

Neutral endopeptidase (NEP) is an enzyme responsible for the metabolism of atrial natriuretic peptide (ANP). Inhibition of NEP results in increased ANP concentrations, which in turn leads to natriuresis, diuresis and decreases in intravascular volume, venous return and blood pressure. ANP is released by atrial myocytes in response to atrial stretch or increased intravascular volume. Elevated plasma concentrations of ANP have been demonstrated as a potential compensatory mechanism in various disease states, including congestive heart failure, renal failure, essential hypertension and cirrhosis.

The secretion of ANP by atrial myocytes causes vasodilation, diuresis, natriuresis, and the inhibition of renin release and aldosterone secretion. In contrast, angiotensin II results in vasoconstriction, sodium and water reabsorption, and aldosterone production. These two hormonal systems interact in a reciprocal or counterbalancing manner to maintain normal physiologic vascular and hemodynamic responses.

U.S. Pat. No. 5,430,145 discloses tricyclic mercaptoacetylamide derivatives useful as ACE and NEP inhibitors. The present invention relates to specific compounds covered by the generic disclosure of U.S. Pat. No. 5,430,145 which have surprisingly improved ADME (Absorption, Distribution, Metabolism, Excretion) properties over the compounds exemplified therein.

SUMMARY OF THE INVENTION

Accordingly, the present invention provides a compound of the formula I:

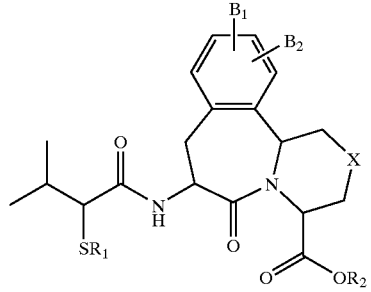

wherein $R_1$ is hydrogen, —$CH_2OC(O)C(CH_3)_3$, or an acyl group;
$R_2$ is hydrogen; —$CH_2O$—$C(O)C(CH_3)_3$; a $C_1$–$C_4$-alkyl; aryl, aryl-($C_1$–$C_4$-alkyl); or diphenylmethyl;
X is —$(CH_2)_n$ wherein n is an integer 0 or 1, —S—, —O—,

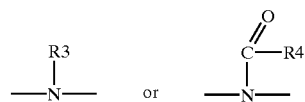

wherein $R_3$ is hydrogen, a $C_1$–$C_4$-alkyl, aryl or aryl-($C_1$–$C_4$-alkyl) and $R_4$ is —$CF_3$, $C_1$–$C_{10}$-alkyl, aryl, or aryl-($C_1$–$C_4$-alkyl);

$B_1$ and $B_2$ are each independently hydrogen, hydroxy, or —$OR_5$, wherein $R_5$ is $C_1$–$C_4$-alkyl, aryl, or aryl-($C_1$–$C_4$-alkyl) or, where $B_1$ and $B_2$ are attached to adjacent carbon atoms, $B_1$ and $B_2$ can be taken together with said adjacent carbon atoms to form a benzene ring or methylenedioxy.

In one embodiment, the present invention provides a compound of the formula I wherein $R_1$ is acetyl. In another embodiment, the present invention provides a compound of the formula I wherein $R_1$ is hydrogen. In a further embodiment, the present invention provides a compound of the formula I wherein $R_2$ is hydrogen. In a further embodiment, the present invention provides a compound of the formula I wherein $B_1$ and/or $B_2$ are hydrogen. In yet a further embodiment, the present invention provides a compound of the formula I wherein X is —$CH_2$.

In one embodiment, the present invention provides a compound of formula IA:

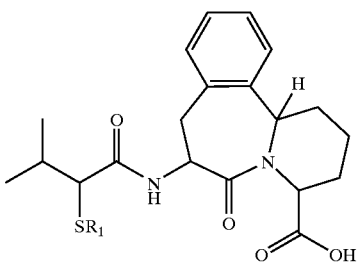

wherein $R_1$ is acetyl or hydrogen.

The structure of preferred embodiments according to the present invention are compounds of the formulae IB and IC below:

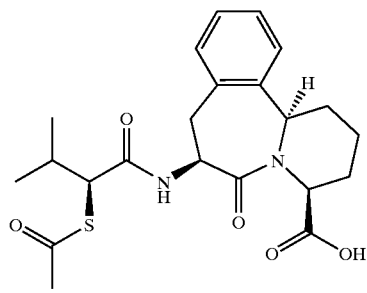

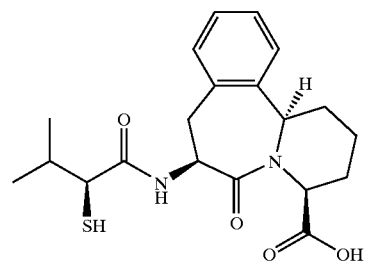

The compounds of the formula I, including compounds of the formulae IA, IB and IC, are particularly useful as dual inhibitors of ACE and NEP.

The present invention accordingly provides a pharmaceutical composition comprising an effective ACE and/or NEP inhibiting amount of a compound of formula I in admixture or otherwise in association with one or more pharmaceutically acceptable carriers or excipients.

DETAILED DESCRIPTION OF THE INVENTION

As used herein, the term '$C_1$–$C_4$-alkyl' refers to a saturated straight or branched monovalent hydrocarbon chain of one, two, three or four carbon atoms and includes methyl, ethyl, propyl, isopropyl, n-butyl, isobutyl, tertiary butyl, and the like groups. The term '$C_1$–$C_{10}$-alkyl' refers to a saturated straight or branched monovalent hydrocarbon chain of one to ten carbon atoms and includes methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like groups.

As used herein 'aryl' refers to a phenyl or naphthyl group unsubstituted or substituted with from one to three substituents selected from the group consisting of methylenedioxy, hydroxy, $C_1$–$C_4$-alkoxy, fluoro and chloro. Included within the scope of the term 'aryl-($C_1$–$C_4$-alkyl)' are phenylmethyl (benzyl), phenylethyl, p-methoxybenzyl, p-fluorobenzyl and p-chlorobenzyl.

As used herein, '$C_1$–C4-alkoxy' refers to a monovalent substitutent which consists of a straight or branched alkyl chain having from 1 to 4 carbon atoms linked through an ether oxygen atom and having its free valence bond from the ether oxygen, and includes methoxy, ethoxy, propoxy, isopropoxy, butoxy, sec-butoxy, tert-butoxy and the like groups.

As used herein, 'heterocycle' means any closed-ring moiety in which one or more of the atoms of the ring are an element other than carbon and includes, but is not limited to, the following: piperidinyl, pyridinyl, isoxazolyl, tetrahydrofuranyl, pyrrolidinyl, morpholinyl, piperazinyl, benzimidazolyl, thiazolyl, thienyl, furanyl, indolyl, 1,3-benzodioxolyl, tetrahydropyranyl, imidazolyl, tetrahydrothienyl, pyranyl, dioxanyl, pyrrolyl, pyrimidinyl, pyrazinyl, thiazinyl, oxazolyl, purinyl, quinolinyl and isoquinolinyl.

As used herein, 'halogen' or 'Hal' refers to a member of the family of fluorine, chlorine, bromine or iodine.

As used herein, 'acyl group' refers to aliphatic and aromatic acyl groups and those derived from heterocyclic compounds. For example, the acyl group may be a lower or ($C_1$–$C_4$)alkanoyl group such as formyl or acetyl, an aroyl group such as benzoyl or a heterocyclic acyl group comprising one or more of the heteroatoms O, N and S, such as the group

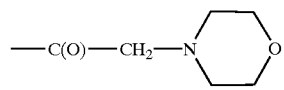

As used herein, 'stereoisomer' is a general term used for all isomers of individual molecules that differ only in the orientation of their atoms in space. The term stereoisomer includes mirror image isomers (enantiomers), geometric (cis/trans or E/Z) isomers, and isomers of compounds with more than one chiral center that are not mirror images of one another (diastereoisomers).

As used herein, 'R' and 'S' are used as commonly used in organic chemistry to denote specific configuration of a chiral center. The term 'R' (rectus) refers to that configuration of a chiral center with a clockwise relationship of group priorities (highest to second lowest) when viewed along the bond toward the lowest priority group. The term 'S' (sinister) refers to that configuration of a chiral center with a counterclockwise relationship of group priorities (highest to second lowest) when viewed along the bond toward the lowest priority group. The priority of groups is based upon sequence rules wherein prioritization is first based on atomic number (in order of decreasing atomic number). A listing and discussion of priorities is contained in *Stereochemistry of Organic Compounds*, Ernest L. Eliel, Samuel H. Wilen and Lewis N. Mander, editors, Wiley-Interscience, John Wiley & Sons, Inc., New York, 1994.

In addition to the (R)-(S) system, the older D-L system may also be used herein to denote absolute configuration, especially with reference to amino acids. In this system a Fischer projection formula is oriented so that the number 1 carbon of the main chain is at the top. The prefix 'D' is used to represent the absolute configuration of the isomer in which the functional (determing) group is on the right side of the carbon at the chiral center and 'L', that of the isomer in which it is on the left.

As used herein, 'treat' or 'treating' means any treatment, including but not limited to, alleviating symptoms, eliminating the causation of the symptoms either on a temporary or permanent basis, or to preventing or slowing the appearance of symptoms and progression of the named disease, disorder or condition.

As described herein, the term 'patient' refers to a warm blooded animal such as a mammal which is afflicted with a particular disease, disorder or condition. It is explicitly understood that guinea pigs, dogs, cats, rats, mice, horses, cattle, sheep, and humans are examples of animals within the scope of the meaning of the term.

As used herein, the term 'pharmaceutically acceptable salt' is intended to apply to any salt, whether previously known or future discovered, that is used by one skilled in the art that is a non-toxic organic or inorganic addition salt which is suitable for use as a pharmaceutical. Illustrative bases which form suitable salts include alkali metal or alkaline-earth metal hydroxides such as sodium, potassium, calcium or magnesium hydroxides; ammonia and aliphatic, cyclic or aromatic amines such as methylamine, dimethylamine, triethylamine, diethylamine, isopropyldiethylamine, pyridine and picoline. Illustrative acids which form suitable salts include inorganic acids such as, for example, hydrochloric, hydrobromic, sulfuric, phosphoric and like acids, and organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids, and organic sulfonic acids such as methanesulfonic and p-toluenesulfonic acids.

As used herein, 'pharmaceutical carrier' refers to known pharmaceutical excipients useful in formulating pharmaceutically active compounds for administration, and which are substantially nontoxic and nonsensitizing under conditions of use. The exact proportion of these excipients is determined by the solubility and chemical properties of the active compound, the chosen route of administration as well as standard pharmaceutical practice.

CHEMICAL SYNTHESES

Compounds according to the present invention may be prepared as follows.

The tricyclic moiety of the compounds of the formula I may be prepared utilizing procedures and techniques well known and appreciated by one of ordinary skill in the art. U.S. Pat. No. 5,430,145 describes examples of suitable procedures and the content of this document is incorporated herein by reference. One such procedure, as illustrated in Scheme A, is described below:

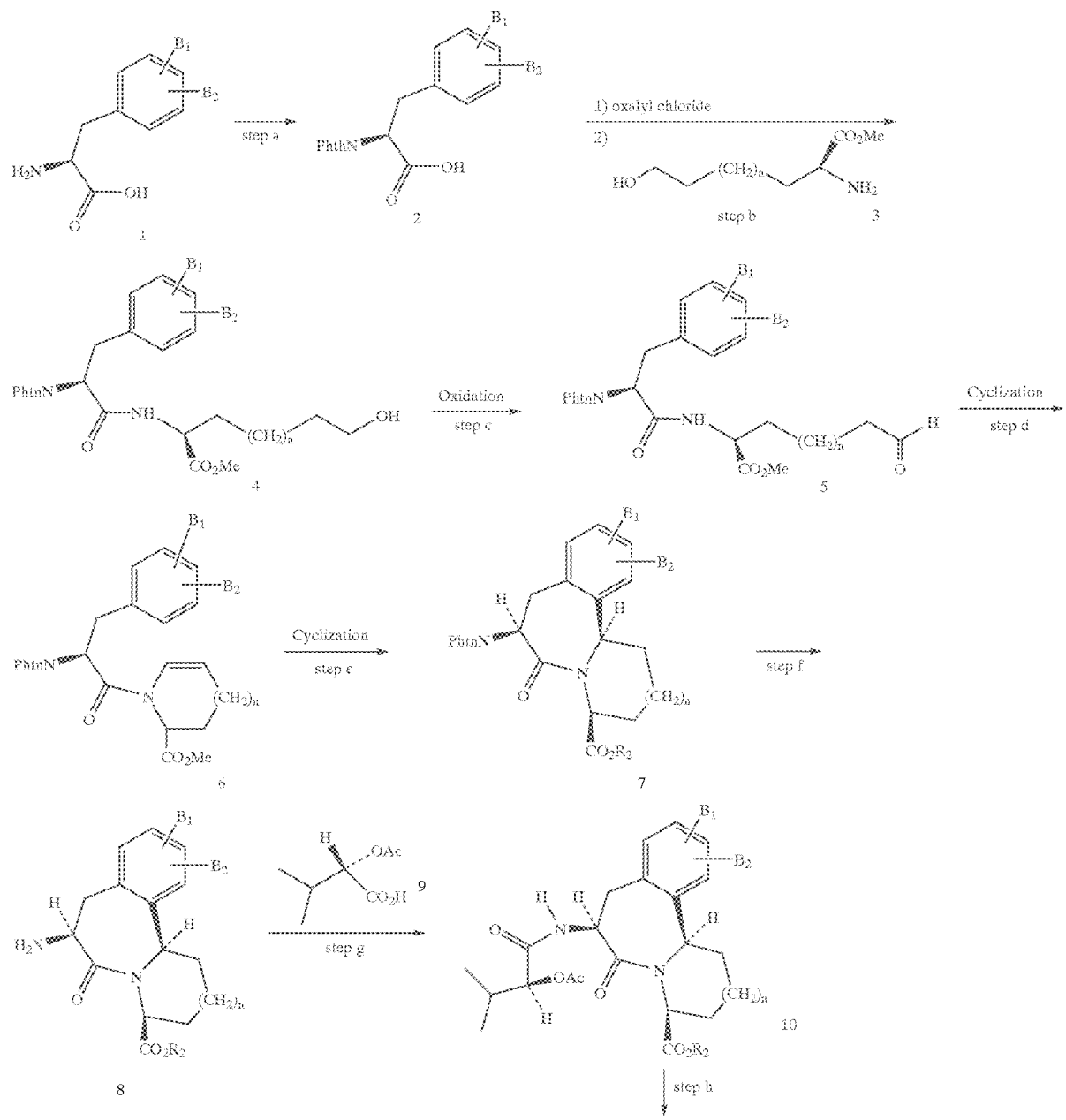

-continued

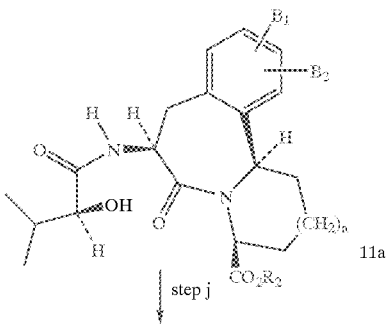
11a

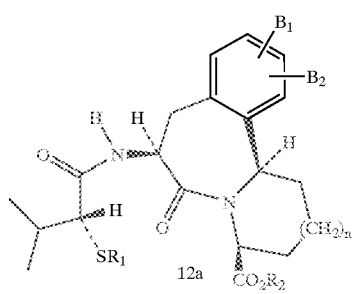
12a

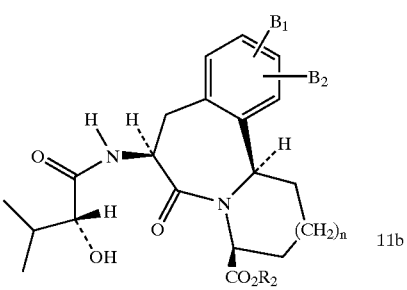
11b

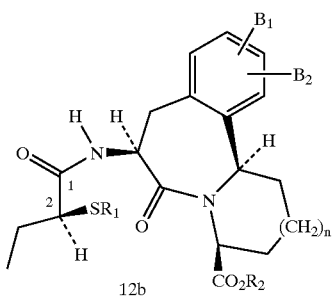
12b

R₁ = COCH₃, COPh
R₂ = CHPh₂

In step a, the appropriate phthalimide blocked (S)-phenylalanine derivative of structure 2 can be prepared by reacting the appropriate (S)-phenylalanine derivative of structure 1 with phthalic anhydride in a suitable aprotic solvent, such as dimethylformamide.

In step b, the appropriate phthalimide blocked (S)-phenylalanine derivative of structure 2 can be converted to the corresponding acid chloride, then reacted with the appropriate amino acid methyl ester of structure 3 in a coupling reaction. For example, the appropriate phthalimide blocked (S)-phenylalanine derivative of structure 2 can be reacted with oxalyl chloride in a suitable aprotic solvent, such as methylene chloride. The resulting acid chloride can then be coupled with the appropriate amino acid methyl ester of structure 3 using a suitable base, such as N-methylmorpholine in a suitable aprotic solvent, such as dimethylformamide, to give the appropriate 1-oxo-3-phenylpropyl-amino acid methyl ester derivative of structure 4.

In step c, the hydroxymethylene functionality of the appropriate 1-oxo-3-phenylpropyl-amino acid methyl ester derivative of structure 4 can be oxidized to the appropriate aldehyde of structure 5 by oxidation techniques well known and appreciated in the art. For example, the hydroxymethylene functionality of the appropriate 1-oxo-3-phenylpropyl-amino acid methyl ester derivative of structure 4 can be oxidized to the appropriate aldehyde of structure 5 by means of a Swern oxidation using oxalyl chloride and dimethylsulfoxide in a suitable aprotic solvent, such as methylene chloride.

In step d, the appropriate aldehyde of structure 5 can be cyclized to the appropriate enamine of structure 6 by acid catalysis. For example, the appropriate aldehyde of structure 5 can be cyclized to the appropriate enamine of structure 6 by treatment with trifluoroacetic acid in a suitable aprotic solvent, such as methylene chloride.

In step e, the appropriate enamine of structure 6 can be converted to the corresponding tricyclic compound of structure 7 by an acid catalyzed Friedel-Crafts reaction. For example, the appropriate enamine of structure 6 can be converted to the corresponding tricyclic compound of structure 7 by treatment with a mixture of trifluoromethane sulfonic acid and trifluoroacetic anhydride in a suitable aprotic solvent, such as methylene chloride.

In step e, it may be necessary to reesterify the carboxy functionality due to the conditions of the work-up. For example, treatment of the crude product with bromodiphenylmethane in a suitable aprotic solvent, such as dimethylformamide along with a non-nucleophilic base, such as cesium carbonate, may be used to give the corresponding diphenylmethyl ester.

In step f, the phthalimide protecting group of the appropriate tricyclic compound of structure 7 can be removed using techniques and procedures well known in the art. For example, the phthalimide protecting group of the appropriate tricyclic compound of structure 7 can be removed using hydrazine monohydrate in a suitable protic solvent such as methanol, to give the corresponding amino compound of structure 8.

In step g, the appropriate (S)-acetate compound of structure 10 can be prepared by reacting the appropriate amino compound of structure 8 with the appropriate (S)-acetate of structure 9. For example, the appropriate amino compound of structure 8 can be reacted with the appropriate (S)-acetate compound of structure 9 in the presence of a coupling reagent such as EEDQ (1-ethoxycarbonyl-2-ethoxy-1,2-dihydroquinoline), DCC (1,3-dicyclohexylcarbodiimide), or diethylcyanophosponate in a suitable aprotic solvent, such as methylene chloride to give the appropriate (S)-acetoxy compound of structure 10.

In step h, the (S)-acetate functionality of the appropriate amide compound of structure 10 can be hydrolyzed to the corresponding (S)-alcohol of structure 11a with a base, such as lithium hydroxide in a suitable solvent mixture, such as tetrahydrofuran and ethanol.

In step i, the (S)-alcohol functionality of the appropriate amide compound of structure 11a can be converted to the corresponding (R)-thioacetate or (R)-thiobenzoate of structure 12a. For example, the appropriate (S)-alcohol of structure 11a can be treated with thiolacetic acid in a Mitsunobu reaction using triphenylphosphine and DIAD (diisopropylazodicarboxylate) in a suitable aprotic solvent, such as tetrahydrofuran.

In step j, the (S)-alcohol functionality of the appropriate amide compound of structure 11a can be converted to the corresponding (R)-alcohol of structure 11b. For example, the appropriate (S)-alcohol of structure 11a can be treated with acetic acid in a Mitsunobu reaction using triphenylphosphine and DIAD in a suitable aprotic solvent, such as tetrahydrofuran. The resulting (R)-acetate can then be hydrolyzed with a suitable base, such as lithium hydroxide.

In step k, the (R)-alcohol functionality of the appropriate amide compound of structure 11b can be converted to the corresponding (S)-thioacetate or (S)-thiobenzoate of structure 12b. For example, the appropriate (R)-alcohol of structure 11b can be treated with thiolacetic acid in a Mitsunobu reaction using triphenylphosphine and DIAD in a suitable aprotic solvent, such as tetrahydrofuran.

As summarized in Table 1, the $R_1$ and $R_2$ groups on the compounds of structures 12a and 12b can be manipulated using techniques and procedures well known and appreciated by one of ordinary skill in the art to give the corresponding compounds of structures 13a–14a and 13b–14b.

For example, the diphenylmethyl ester functionality of the appropriate compound of structure 12a can be removed using trifluoroacetic acid to give the appropriate carboxylic acid compound of structure 13a. Similarly, the diphenylmethyl ester functionality of the appropriate compound of structure 12b can be removed using trifluoroacetic acid to give the carboxylic acid compound of structure 13b.

The (R)-thioacetate or (R)-thiobenzoate functionality of the appropriate compound of structure 13a can be removed with lithium hydroxide in a suitable solvent mixture such as tetrahydrofuran and ethanol to give the appropriate (R)-thio compound of structure 14a. Similarly, the (S)-thioacetate or (S)-thiobenzoate functionality of the appropriate compound of structure 13b can be removed with lithium hydroxide in a suitable solvent mixture such as tetrahydrofuran and ethanol to give the appropriate (S)-thio compound of structure 14b.

TABLE 1

MANIPULATION OF $R_1$ AND $R_2$

| Compound | $R_1$ | $R_2$ |
| --- | --- | --- |
| 13a and 13b | COCH$_3$ or COPh | H |
| 14a and 14b | H | H |

Although the general procedures outlined in Scheme A show the preparation of the compounds of the formula I wherein the group —COOR$_2$ is of the (S)-configuration, the compounds of the formula I wherein the group —COOR$_2$ is of the (R)-configuration may be prepared by analogous procedures by substituting an appropriate (R)-amino acid methyl ester for the (S)-amino acid methyl ester of structure 3 in step b.

Starting materials for use in the general synthetic procedures outlined in Scheme A are readily available to one of ordinary skill in the art. For example, certain (R)- and (S)-carboxy acetate or benzoate starting materials of structure 9 can be prepared by stereoselective reduction of the corresponding pyruvate compounds with alpine boranes as described in *J. Org. Chem.* 47, 1606 (1982), *J. Org. Chem.* 49, 1316 (1984), and *J. Am. Chem. Soc.* 106, 1531 (1984), followed by treating the resulting alcohol with acetic anhydride or benzoic anhydride to give the corresponding (R)- or (S)-carboxy acetate or benzoate compounds of structure 9.

Alternatively, certain tricyclic compounds of structure 7 may be prepared as described in European patent application EP 249223 A.

The present invention provides a process for the preparation of a compound of the formula I above, comprising reacting a compound of the formula II

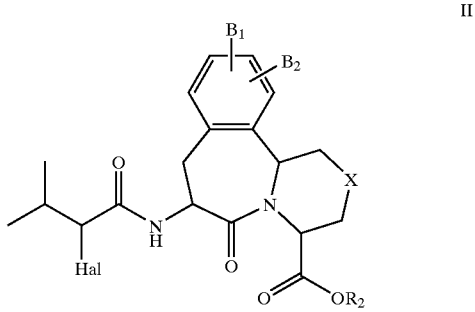

II where $R_2$, X, $B_1$ and $B_2$ are as previously defined and Hal is halogen, with a compound of the formula $R_1SH$, where $R_1$ is as previously defined, in the presence of a base, such as an alkali metal carbonate.

The present invention furthermore provides a process for the preparation of a compound of the formula II, comprising reacting a compound of the formula III

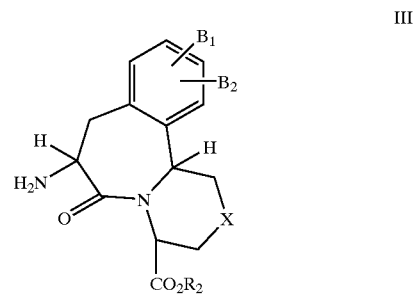

III wherein $R_2$, X, $B_1$ and $B_2$ are as previously defined with a compound of the formula IV

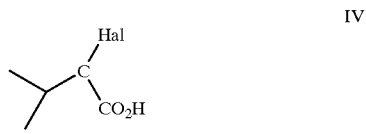

IV where Hal is halogen.

An alternative process for the preparation of a compound of the formula I according to the present invention comprises reacting a compound of the formula III

III

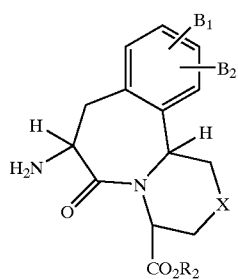

wherein $R_2$, X, $B_1$ and $B_2$ are as previously defined, with a compound of the formula V

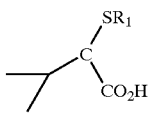

wherein $R_1$ is as previously defined.

In the latter process, the appropriate amino compound of the formula III may be reacted with the appropriate (S)- or (R)-thioacetate of the formula V to give the corresponding (S)- or (R)-thioacetate, respectively, of the formula I as described previously in Scheme A, step g.

Scheme B provides another general synthetic procedure for preparing compounds of the formula I.

Scheme B

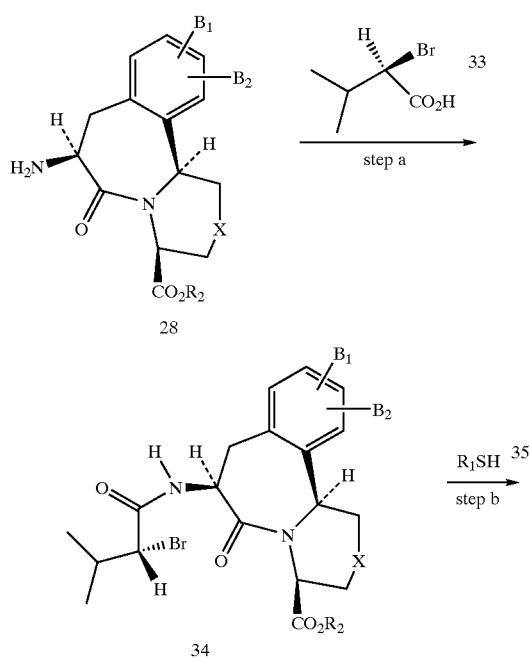

-continued

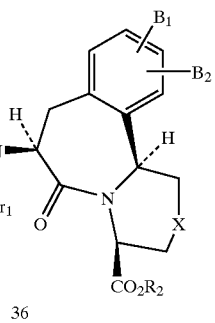

36

$R_1$ = $COCH_3$, COPh
X = O, S, NH or $(CH_2)n$
n = 0 or 1

In step a, the appropriate amino compound of structure 28 wherein X is O, S, NH or $(CH_2)_n$ wherein n is 0 or 1 is reacted with the appropriate (R)-bromoacid of structure 33 to give the corresponding (R)-bromoamide compound of structure 34 wherein X is O, S, NH or $(CH_2)_n$ wherein n is 0 or 1 under similar conditions as described previously in Scheme A, step g.

Alternatively, the appropriate amino compound of structure 28 wherein X is O, S, NH or $(CH_2)_n$ wherein n is 0 or 1 is reacted with the appropriate (S)-bromoacid to give the corresponding (S)-bromoamide wherein X is O, S, NH or $(CH_2)_n$ wherein n is 0 or 1, or the appropriate amino compound of structure 28 wherein X is O, S, NH or $(CH_2)_n$ wherein n is 0 or 1 is reacted with the appropriate enantiomeric mixture of the bromoacid to give the corresponding diastereoisomeric mixture of the bromoamide wherein X is O, S, NH or $(CH_2)_n$ wherein n is 0 or 1 as described previously in Scheme A, step g.

In step b, the (R)-bromo functionality of the appropriate (R)-bromoamide compound of structure 34 wherein X is O, S, NH or $(CH_2)_n$ wherein n is 0 or 1 is converted to the corresponding (S)-thioacetate or (S)-thiobenzoate of structure 36, wherein X is O, S, NH or $(CH_2)_n$ wherein n is 0 or 1.

Alternatively, the (S)-bromo functionality of the appropriate (S)-bromoamide wherein X is O, S, NH or $(CH_2)_n$ wherein n is 0 or 1 is converted to the corresponding (R)-thioacetate or (R)-thiobenzoate wherein X is O, S, NH or $(CH_2)_n$ wherein n is 0 or 1.

For example, the appropriate (R)-bromoamide compound of structure 34 wherein X is O, S, NH or $(CH_2)_n$ wherein n is 0 or 1 is reacted with thiolacetic acid or thiolbenzoic acid of structure 35 in the presence of a base, such as cesium or sodium carbonate. The reactants are typically contacted in a suitable organic solvent such as a mixture of dimethylformamide and tetrahydrofuran. The reactants are typically stirred together at room temperature for a period of time ranging from 1 to 8 hours. The resulting (S)-thioacetate or (S)-thiobenzoate of structure 36 wherein X is O, S, NH or $(CH_2)_n$ wherein n is 0 or 1 is recovered from the reaction zone by extractive methods as is known in the art. It may be purified by chromatography.

Alternatively, the bromo functionality of the appropriate diastereoisomeric mixture of the bromoamides described supra wherein X is O, S, NH or $(CH_2)_n$ wherein n is 0 or 1 is converted to the corresponding diastereoisomeric mixture of thioacetate or thiobenzoate compounds wherein X is O, S, NH or $(CH_2)_n$ wherein n is 0 or 1.

Although Scheme B provides for the preparation of compounds of formula I wherein the tricyclic moiety has a 4-carboxy functionality of the (S)-configuration when for example X is —CH$_2$, the compounds of formula I wherein the carboxy functionality is of the (R)-configuration may be prepared by substituting the appropriate (4R)-carboxy amino compound for the amino compound of structure 28 whose preparation is described in Scheme A.

EXPERIMENTAL

The following Examples present typical syntheses as described in Scheme B. These Examples are understood to be illustrative only and are not intended to limit the scope of the present invention in any way. As used herein, the following terms have the indicated meanings: 'g' refers to grams; 'mmol' refers to millimoles; 'ml' refers to milliliters; '° C.' refers to degrees Celsius.

EXAMPLE 1
Preparation of (R)-2-Bromo-3-methylbutanoic Acid (Structure 33)

To a cooled solution of D-valine (12.7 g, 100 mmol) in 100 ml 2.5N sulfuric acid and 49% HBr (33 g, 200 mmol) at −10° C. was added sodium nitrite (6.90 g, 100 mmol) in 50 ml water over a period of 30 minutes. Stirring between −5° C. and −10° C. was maintained for an additional 3 hours. The reaction mixture was extracted with 2×150 ml of methylene chloride, dried over MgSO$_4$ and concentrated to give a light amber oil (9.7 g, 50%, 53.6 mmol).

EXAMPLE 2
Preparation of [4S-[4α,7α(S),12bβ]]-7-[[2(S)-acetylthio-3-methyl-1-oxobutyl]amino]-1,2,3,4,6,7,8,12b-octahydro-6-oxo-pyrido[2,1a][2]benzazepine-4-carboxylic Acid, Diphenylmethyl Ester Scheme B, step a: [4S-[4α,7α(S),12bβ]]-7-[[2(R)-bromo-3-methyl-1-oxobutyl]amino]-1,2,3,4,6,7,8,12b-octahydro-6-oxo-pyrido[2,1a][2]benzazepine-4-carboxylic acid, diphenylmethyl ester (R)-2-Bromo-3-methylbutanoic acid (900 mg, 5.0 mmol) and [4S-[4α,7α(S),12bβ]]-7-(amino)-1,2,3,4,6,7,8,12b-octahydro-6-oxo-pyrido[2,1a][2]benzazepine-4-carboxylic acid, diphenylmethyl ester (1.76 g, 4.0 mmol) were dissolved in dry methylene chloride (5 ml) and treated with 1-(3-dimethylaminopropyl)-3-ethylcarbodiimide (EDC, 1.0 g, 5.0 mmol) at 25° C. for 2 hours. After 18 hours only a trace of [4S-[4α,7α(S), 12bβ]]-7-(amino)-1,2,3,4,6,7,8,12b-octahydro-6-oxo-pyrido[2,1a][2]-benzazepine-4-carboxylic acid, diphenylmethyl ester remained. The mixture was diluted with methylene chloride (75 ml), washed with 10% hydrochloric acid and saturated with sodium hydrogen carbonate. The mixture was then dried (MgSO$_4$), concentrated in vacuo and purified by flash chromatography to give the title compound (C$_{33}$H$_{35}$N$_2$O$_4$Br) (2.4 g, 4.0 mmol)

Scheme B, step b: [4S-[4α,7α(S),12bβ]]-7-[[2(S)-acetylthio-3-methyl-1-oxobutyl]amino]-1,2,3,4,6,7,8,12b-octahydro-6-oxo-pyrido[2,1a][2]benzazepine-4-carboxylic acid, diphenylmethyl ester Thiolacetic acid (456 mg, 6.0 mmol) and cesium carbonate (325.8 mg, 3.0 mmol) were dissolved in methanol (5 ml) under a nitrogen atmosphere and evaporated to dryness. The evaporated product from step a (4.0 mmol), dissolved in 5 ml of dry dimethylformamide, was added to the mixture followed by stirring under a nitrogen atmosphere for 2 hours. The mixture was partitioned between ethyl acetate (100 ml) and brine, washed with 10% HCl and saturated sodium hydrogen carbonate, dried (MgSO$_4$), filtered and concentrated to give the crude product (2.2 g) as a light yellow foam. The product was dissolved in methylene chloride and purified by chromatography (25% ethyl acetate/hexane) on 200 ml silica using 20% ethyl acetate. The fractions were combined and concentrated to give the title ester compound (2.15 g).

EXAMPLE 3
Preparation of [4S-[4α,7α(S),12bβ]]-7-[[2(S)-acetylthio-3-methyl-1-oxobutyl]amino]-1,2,3,4,6,7,8,12b-octahydro-6-oxo-pyrido[2,1a][2]benzazepine-4-carboxylic Acid.

The crude product produced in Example 2 (3.5 mmol) was dissolved in methylene chloride (6.0 ml) and anisole (1.0 ml), cooled to −50° C. and treated with trifluoroacetic acid (6.0 ml). The mixture was allowed to warm to 25° C., stirred for 2 hours, concentrated in vacuo and purified by chromatography (1:1 ethyl acetate/hexane plus 1% acetic acid) to give the title compound.

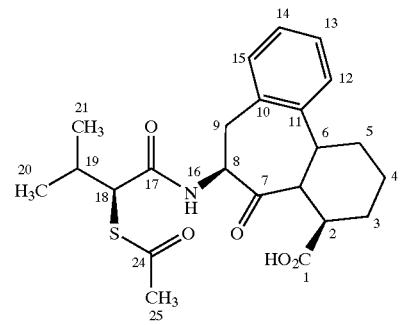

Molecular Weight=432.54
Molecular Formula=C$_{22}$H$_{28}$N$_2$O$_5$S $^1$H- and $^{13}$C- NMR data for MDL107688 (DMSO-d$_6$, 300 K, numbering not according to IUPAC rules)

| Position | $^{13}$C (ppm) | $^1$H (ppm) |
|---|---|---|
| 1 | 171.79 | — |
| 1-COOH | — | 12.07 |
| 2 | 50.53 | 4.99 m |
| 3 | 24.98 | 2.21 m, 1.69 m |
| 4 | 16.93 | 1.67 m, 1.67 m |
| 5 | 24.69 | 2.38 m, 1.92 m |
| 6 | 49.78 | 5.60 |
| 7 | 171.37 | — |
| 8 | 48.10 | 5.60 |
| 9 | 35.60 | 3.22 dd, 2.97 dd |
| 10 | 136.72 | — |
| 11 | 136.89 | — |
| 12 | 124.83 | 7.19 d |
| 13 | 125.21 | 7.08 t |
| 14 | 126.67 | 7.13 t |
| 15 | 130.10 | 7.07 d |
| 16 | — | 8.33 d |
| 17 | 169.11 | — |
| 18 | 53.82 | 4.12 d |
| 19 | 30.69 | 2.14 m |
| 20* | 20.18 | 0.99 d |
| 21* | 19.29 | 0.94 d |
| 24 | 194.36 | — |
| 25 | 30.34 | 2.36 s |

*no clear differentiation between position 20 and 21

EXAMPLE 4
Preparation of [4S-[4α,7α(S),12bβ]]-7-[[3-methyl-1-oxo-2(S)-thiobutyl]amino]1,2,3,4,6,7,8,12b-octahydro-6-oxo-pyrido[2,1a][2]benzazepine-4-carboxylic Acid.

The product obtained in Example 3 (75 mg, 0.17 mmol) was dissolved in 1.0 ml of degassed methanol under nitrogen atmosphere and treated with lithium hydroxide (0.4 ml of a 1N solution). After stirring at 25° C. for 1.5 hours, the solution was concentrated in vacuo, diluted with water (2 ml) and acidified with hydrochloric acid (0.5 ml of a 1N solution). The resultant product was filtered and vacuum dried to give the title compound as a white solid (55 mg, 0.14 mmol, 83%).

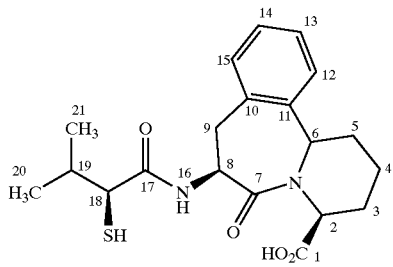

Molecular Weight=390.50
Molecular Formula=$C_{20}H_{26}N_2O_4S$ $^1$H- and $^{13}$C- NMR data for MDL108048 (DMSO-$d_6$, 300 K, numbering not according to IUPAC rules)

| Position | δ ($^{13}$C) | m ($^{13}$C) | δ($^1$H) | $^nJ_{CH}$ |
|---|---|---|---|---|
| 1 | 171.86 | s | — | 1.68 |
| 2 | 50.63 | d | 4.98 | 5.60, 1.68 |
| 3 | 25.04 | t | 2.23,1.68 | 4.98, 1.65 |
| 4 | 17.00 | t | 1.65 | 4.98, 1.91, 1.68, (5.60) |
| 5 | 24.77 | t | 2.38, 1.91 | 5.60, 1.65 |
| 6 | 49.95 | d | 5.60 | 7.19, 4.98, 1.91 |
| 7 | 171.55 | s | — | 5.63, 3.25, 2.97 |
| 8 | 47.89 | d | 5.632 | 3.25, 2.97 |
| 9 | 36.05 | t | 3.25, 2.97 | 7.07, 5.63 |
| 10 | 136.86* | s | — | 3.25, 2.97, 5.63, 7.19 |
| 11 | 138.82* | s | — | 5.63, 7.08, 3.25, 2.97 |
| 12 | 124.87 | d | 7.185 | 7.13, 5.60, (3.25), (2.97) |
| 13 | 125.31 | d | 7.084 | 7.07, (3.25), (2.97) |
| 14 | 126.70 | d | 7.127 | 7.19 |
| 15 | 130.11 | d | 7.073 | 7.08, 3.25, 2.97 |
| 16 | NH | — | 8.30 | 5.63 |
| 17 | 171.29 | s | — | 8.30, 3.33, 1.94 |
| 18 | 48.85 | d | 3.326 | 1.94, 0.98, 0.94 |
| 19 | 32.46 | d | 1.936 | 3.33, 0.99, 0.94 |
| 20 | 19.32 | q | 0.987 | 0.94, 1.94, 3.33 |
| 21 | 20.58 | q | 0.944 | 0.99, 1.94, 3.33 |

*no clear differentiation between position 20 and 21

The compounds according to the present invention can be used to treat warm-blooded animals or mammals, including mice, rats and humans, suffering from disease states such as, but not limited to, hypertension, congestive heart failure, cardiac hypertrophy, renal failure, and/or cirrhosis.

An effective ACE and NEP inhibitory amount of a compound of the formula I is an amount which is effective in inhibiting ACE and NEP which results, for example, in a hypotensive effect.

An effective ACE and NEP inhibitory dose of a compound of the formula I can be readily determined by the use of conventional techniques and by observing results obtained under analogous circumstances. In determining the effective dose, a number of factors are considered including, but not limited to: the species of animal; the animal's size, age and general health; the specific disease involved; the degree of or involvement or the severity of the disease; the response of the individual patient; the particular compound administered; the dose regimen selected; and the use of concomitant medication.

An effective dual ACE and NEP inhibitory amount of a compound of the formula I will generally vary from about 0.01 milligram per kilogram body weight per day (mg/kg/day) to about 20 mg/kg/day. A daily dose of from about 0.1 mg/kg to about 10 mg/kg is preferred.

In effecting treatment of a patient, compounds of Formula I can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the disease state to be treated, the stage of the disease, and other relevant circumstances.

FORMULATIONS

Compounds of formula I can be administered in the form of pharmaceutical compositions or medicaments which are made by combining the compounds of Formula I with pharmaceutically acceptable carriers or excipients, the proportion and nature of which are determined by the chosen route of administration, and standard pharmaceutical practice.

The present invention provides pharmaceutical compositions comprising an effective amount of a compound of Formula I in admixture or otherwise in association with one or more pharmaceutically acceptable carriers or excipients.

The pharmaceutical compositions or medicaments are prepared in a manner well known in the pharmaceutical art. The carrier may be a solid, semi-solid, or liquid material which can serve as a vehicle or medium for the active ingredient. Suitable carriers or excipients are well known in the art. The pharmaceutical composition may be adapted for oral or parental use and may be administered to the patient in the form of tablets, capsules, suppositories, solutions, suspensions, or the like. Suitable pharmaceutical carriers and formulation techniques are found in standard texts, such as *Remington: The Science and Practice of Pharmacy,* 19$^{th}$ edition, Volumes 1 and 2, 1995, Mack Publishing Co., Easton, Pa., U.S.A., which is herein incorporated by reference.

The pharmaceutical compositions may be administered orally, for example, with an inert diluent or with an edible carrier. They may be enclosed in gelatine capsules or compressed into tablets. For the purpose of oral therapeutic administration, the compounds of Formula I may be incorporated with excipients and used in the form of tablets, troches, capsules, elixirs, suspensions, syrups, wafers, chewing gums and the like. These preparations should contain at least 4% of the compound of Formula I, the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatine; excipients, such as starch or lactose, disintegrating agents such as alginic acid, Primojel®;, corn starch and the like; lubricants, such as magnesium stearate or Sterotex®; glidants, such as colloidal silicon dioxide; and sweetening agents, such as sucrose or saccharin may be added or flavouring agents, such as peppermint, methyl salicylate or orange flavouring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colourings and flavours. Materials used in preparing these various compositions should be pharmaceutically pure and non toxic in the amounts used.

For the purpose of parenteral administration, the compounds of Formula I may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained. The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite, chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

It is, of course, understood that the compounds of Formula I may exist in a variety of isomeric configurations including structural as well as stereoisomers. It is further understood that the present invention encompasses those compounds of Formula I in each of their various structural and stereoisomeric configurations as individual isomers and as mixtures of isomers.

Biological Methods and Results

The new compounds of the formula I have long-lasting, intensive hypotensive action. Moreover, in patients with heart failure the compounds of the formula I increase cardiac output, decrease Left Ventricular End Diastolic Pressure (LVEDP) and increase coronary flow. The exceptionally powerful activity of the compounds according to the formula I is demonstrated by the pharmacological data summarized in FIG. 1.

The results in FIG. 1 show that there is a significantly improved reduction of mean arterial blood pressure (MAP) at each of the administered doses in comparison to the same oral dose of MDL 100 240.

Data obtained from congestive heart failure models in rats also showed the compounds of the formula I to have significant beneficial effects on cardiac function in comparison to known compounds. For example, in studies in which MDL 100 240 and MDL 107 688 were tested in rats with heart failure, similar efficacy was found when MDL 107 688 was used at half the dose of MDL 100 240.

What is claimed is:
1. A compound of the formula I

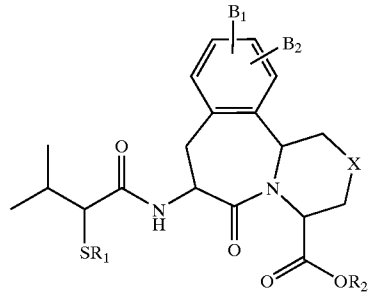

wherein
$R_1$ is hydrogen, —$CH_2OC(O)C(CH_3)_3$, ($C_1$–$C_4$)alkanoyl, benzoyl, or an acyl group of the formula

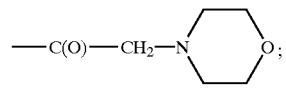

$R_2$ is hydrogen, —$CH_2O$—$C(O)C(CH_3)_3$, a $C_1$–$C_4$-alkyl, aryl, aryl-($C_1$–$C_4$-alkyl) or diphenylmethyl;
X is —$(CH_2)_n$ wherein n is an integer 0 or 1, —S—, —O—,

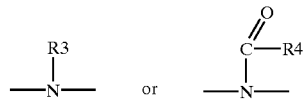

wherein $R_3$ is hydrogen, a $C_1$–$C_4$-alkyl, aryl, or aryl-($C_1$–$C_4$-alkyl) and $R_4$ is —$CF_3$, $C_1$–$C_{10}$-alkyl aryl, or aryl-($C_1$–$C_4$-alkyl);
$B_1$ and $B_2$ are each independently hydrogen, hydroxy, or —$OR_5$, wherein $R_5$ is $C_1$–$C_4$-alkyl, aryl, or aryl-($C_1$–$C_4$-alkyl) or, where $B_1$ and $B_2$ are attached to adjacent carbon atoms, $B_1$ and $B_2$ can be taken together with said adjacent carbon atoms to form a benzene ring or methylenedioxy;
or its pharmaceutically acceptable salts or stereoisomers thereof.
2. The compound according to claim 1 wherein $B_1$ and $B_2$ are hydrogen.
3. The compound according to claim 2 wherein X is —$(CH_2)_n$ and n is 1.
4. The compound according to claim 3 wherein $R_1$ is acetyl or hydrogen.
5. The compound according to claim 4 wherein the compound is [4S-[4α,7α(S),12bβ]]-7-[[2(R)-acetylthio-3-methyl-1-oxobutyl]amino]-1,2,3,4,6,7,8,12b-octahydro-6-oxo-pyrido[2,1a][2]benzazepine-4-carboxylic acid, diphenylmethyl ester.
6. The compound according to claim 4 wherein the compound is [4S-[4α,7α(S), 12bβ]]-7-[[2(S)-acetylthio-3-methyl-1-oxobutyl]amino]-1,2,3,4,6,7,8,12b-octahydro-6-oxo-pyrido[2,1a][2]benzazepine-4-carboxylic acid, diphenylmethyl ester.
7. The compound according to claim 4 wherein the compound is [4S-[4α,7α(S), 12bβ]]-7-[[3-methyl-1-oxo-2(R)-thiobutyl]amino]-1,2,3,4,6,7,8,12b-octahydro-6-oxo-pyrido[2,1a][2]benzazepine-4-carboxylic acid, diphenylmethyl ester.

8. The compound according to claim 4 wherein the compound is [4S-[4α,7α(S),12bβ]]-7-[[3-methyl-1-oxo-2(S)-thiobutyl]amino]-1,2,3,4,6,7,8,12b-octahydro-6-oxo-pyrido[2,1a][2]benzazepine-4-carboxylic acid, diphenylmethyl ester.

9. The compound according to claim 4 wherein $R_2$ is hydrogen.

10. The compound according to claim 9 wherein the compound is [4S-[4α,7α(S), 12bβ]]-7-[[2(R)-acetylthio-3-methyl-1-oxobutyl]amino]-,2,3,4,6,7,8, 2b-octahydro-6-oxo-pyrido[2,1a][2]benzazepine-4-carboxylic acid.

11. The compound according to claim 9 wherein the compound is [4S-[4α,7α(S), 12bβ]]-7-[[2(S)-acetylthio-3-methyl-1-oxobutyl]amino]-1,2,3,4,6,7,8,12b-octahydro-6-oxo-pyrido[2,1a][2]benzazepine-4-carboxylic acid.

12. The compound according to claim 9 wherein the compound is [4S-[4α,7α(S), 12bβ]]-7-[[3-methyl-1-oxo-2(R)-thiobutyl]amino]-1,2,3,4,6,7,8, 12b-octahydro-6-oxo-pyrido[2,1a][2]benzazepine-4-carboxylic acid.

13. The compound according to claim 9 wherein the compound is [4S-[4α,7α(S), 12bβ]]-7-[[3-methyl-1-oxo-2(S)-thiobutyl]amino]-1,2,3,4,6,7,8,12b-octahydro-6-oxo-pyrido[2,1a][2]benzazepine-4-carboxylic acid.

14. A process for the preparation of a compound of the formula I

I wherein $R_1$ is hydrogen, —$CH_2OC(O)C(CH_3)_3$, ($C_1$–$C_4$) alkanoyl benzoyl, or an acyl group of the formula

—C(O)—$CH_2$—N⌒O ;

$R_2$ is hydrogen, —$CH_2O$—$C(O)C(CH_3)_3$, a $C_1$–$C_4$-alkyl, aryl, aryl-($C_1$–$C_4$-alkyl) or diphenylmethyl;

X is —$(CH_2)_n$ wherein n is an integer 0 or 1, —S—, —O—, $$\underset{\underset{\mathrm{N}}{|}}{\overset{R3}{|}} \quad \text{or} \quad \underset{\underset{\mathrm{N}}{|}}{\overset{\overset{O}{\|}}{\underset{|}{C}}-R4}$$

wherein $R_3$ is hydrogen, a $C_1$–$C_4$-alkyl, aryl, or aryl-($C_1$–$C_4$-alkyl) and $R_4$ is —$CF_3$, $C_1$–$C_{10}$-alkyl, aryl, or aryl-($C_1$–$C_4$-alkyl);

$B_1$ and $B_2$ are each independently hydrogen, hydroxy, or —$OR_5$, wherein $R_5$ is $C_1$–$C_4$-alkyl, aryl, or aryl-($C_1$–$C_4$-alkyl), or, where $B_1$ and $B_2$ are attached to adjacent carbon atoms, $B_1$ and $B_2$ can be taken together with said adjacent carbon atoms to form a benzene ring or methylenedioxy;

comprising the step of reacting a compound of the formula II

II wherein Hal is halogen, with a compound of the formula $R_1SH$, wherein $R_1$ is as previously defined, in the presence of a base.

15. A process for the preparation of a compound of the formula II:

II wherein

Hal is halogen;

$R_2$ is hydrogen, —$CH_2O$—$C(O)C(CH_3)_3$, a $C_1$–$C_4$-alkyl, aryl, aryl-($C_1$–$C_4$-alkyl), or diphenylmethyl;

X is —$(CH_2)_n$ wherein n is an integer 0 or 1, —S—, —O—, $$\underset{\underset{\mathrm{N}}{|}}{\overset{R3}{|}} \quad \text{or} \quad \underset{\underset{\mathrm{N}}{|}}{\overset{\overset{O}{\|}}{\underset{|}{C}}-R4}$$

wherein $R_3$ is hydrogen, a $C_1$–$C_4$-alkyl, aryl, or aryl-($C_1$–$C_4$-alkyl), and $R_4$ is —$CF_3$, $C_1$–$C_{10}$-alkyl, aryl, or aryl-($C_1$–$C_4$-alkyl);

$B_1$ and $B_2$ are each independently hydrogen, hydroxy, or —$OR_5$, wherein $R_5$ is $C_1$–$C_4$-alkyl, aryl, or aryl-($C_1$–$C_4$-alkyl), or, where $B_1$ and $B_2$ are attached to adjacent carbon atoms, $B_1$ and $B_2$ can be taken together with said adjacent carbon atoms to form a benzene ring or methylenedioxy;

comprising the step of reacting a compound of the formula III

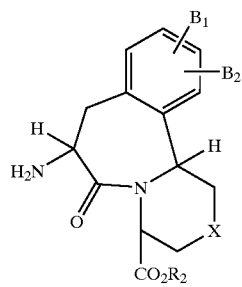

wherein $R_2$, X, $B_1$ and $B_2$ are as previously defined with a compound of the formula IV

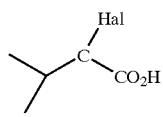

wherein Hal is halogen.

16. A method of treating a disease state comprising administering to a patient in need of said treatment a therapeutically effective angiotensin converting enzyme and neutral endopeptidase inhibitory amount of a compound according to claim 1, wherein said disease state is selected from the group consisting of hypertension, congestive heart failure, cardiac hypertrophy and cirrhosis.

17. The method according to claim 16 wherein the disease state is hypertension.

18. The method according to claim 16 wherein the disease state is congestive heart failure.

19. A pharmaceutical composition comprising one or more compounds as set forth in claim 1 and a pharmaceutically acceptable carrier.

20. A method for the preparation of a pharmaceutical composition comprising the step of combining one or more of the compounds as set forth in claim 1 with a pharmaceutically acceptable carrier.

21. The method according to claim 16 wherein the disease state is cardiac hypertrophy.

22. The method according to claim 16 wherein the disease state is cirrhosis.

* * * * *

UNITED STATES PATENT AND TRADEMARK OFFICE
CERTIFICATE OF CORRECTION

PATENT NO. : 6,602,866 B2
DATED : August 5, 2003
INVENTOR(S) : Flynn et al.

It is certified that error appears in the above-identified patent and that said Letters Patent is hereby corrected as shown below:

Column 5,
Line 1, "isopropyidiethylamine" should read -- isopropyldiethylamine --

Columns 5 and 6,
Scheme A, steps a-h, structures appear as:

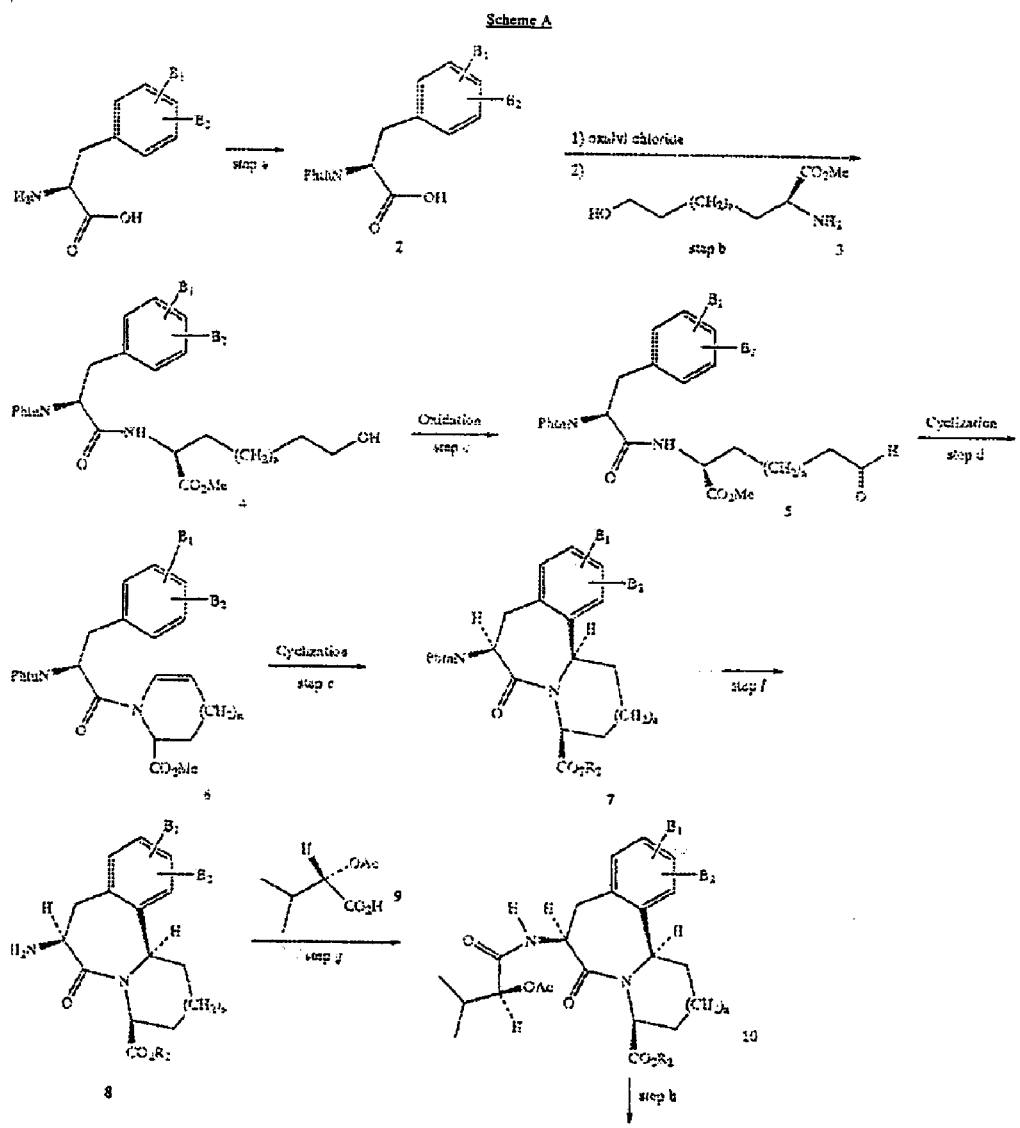

UNITED STATES PATENT AND TRADEMARK OFFICE
CERTIFICATE OF CORRECTION

PATENT NO. : 6,602,866 B2
DATED : August 5, 2003
INVENTOR(S) : Flynn et al.

It is certified that error appears in the above-identified patent and that said Letters Patent is hereby corrected as shown below:

Columns 5 and 6 (continued),
Scheme A, steps a-h, structures should appear as:

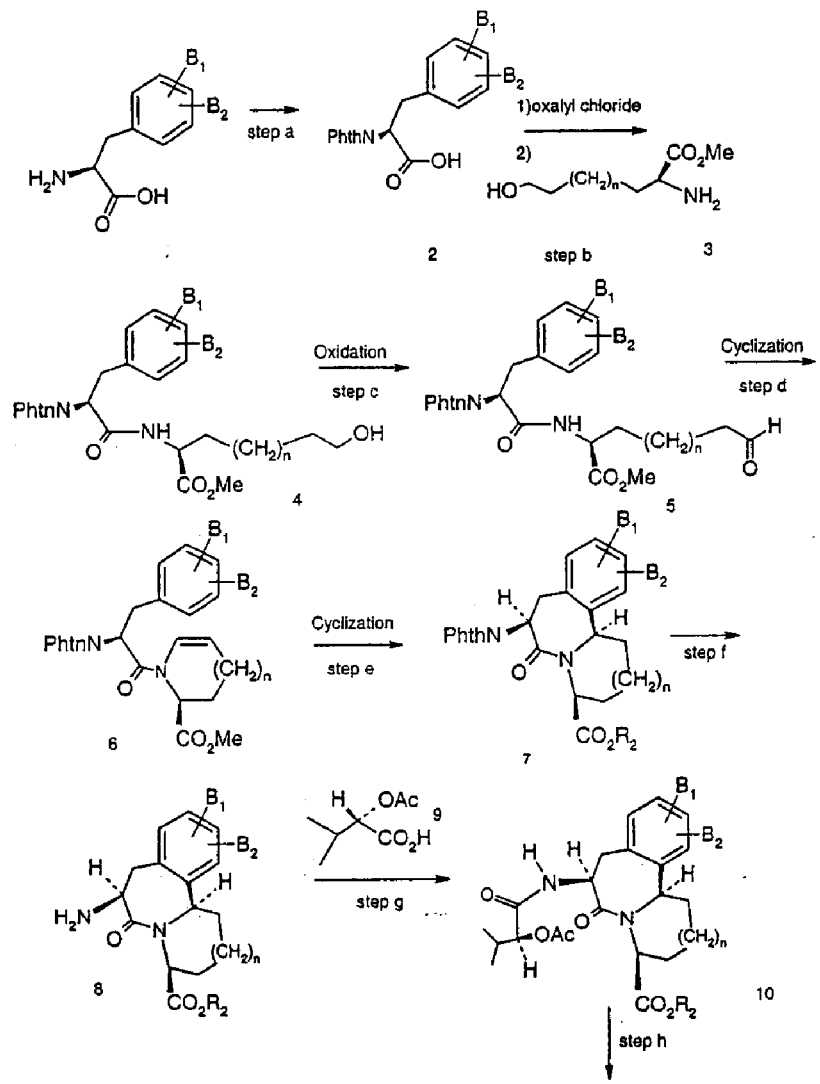

UNITED STATES PATENT AND TRADEMARK OFFICE
CERTIFICATE OF CORRECTION

PATENT NO. : 6,602,866 B2
DATED : August 5, 2003
INVENTOR(S) : Flynn et al.

It is certified that error appears in the above-identified patent and that said Letters Patent is hereby corrected as shown below:

Columns 7 and 8,
Scheme A-cont., steps i, structures appear as:

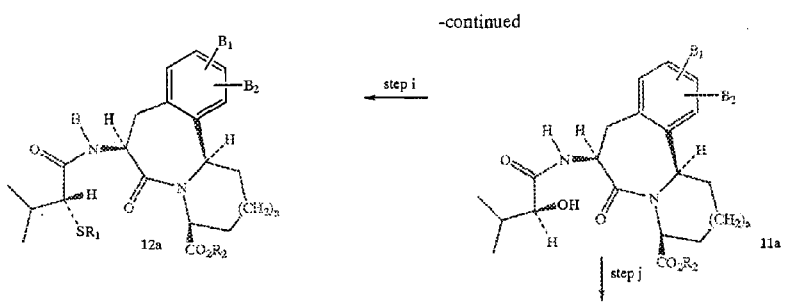

Scheme A-cont., steps i, structures should appear as:

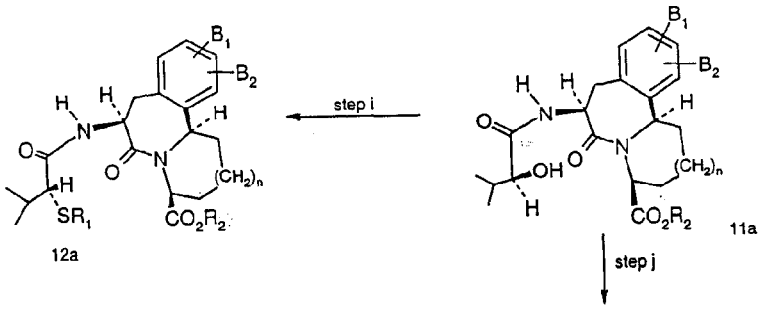

Scheme A-cont., step k, reads as:

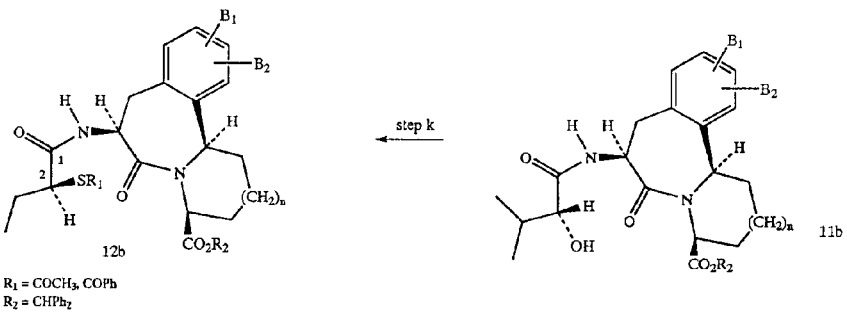

UNITED STATES PATENT AND TRADEMARK OFFICE
CERTIFICATE OF CORRECTION

PATENT NO.   : 6,602,866 B2
DATED        : August 5, 2003
INVENTOR(S)  : Flynn et al.

It is certified that error appears in the above-identified patent and that said Letters Patent is hereby corrected as shown below:

Column 7 and 8 (continued),
Scheme A-cont., step k, should read as:

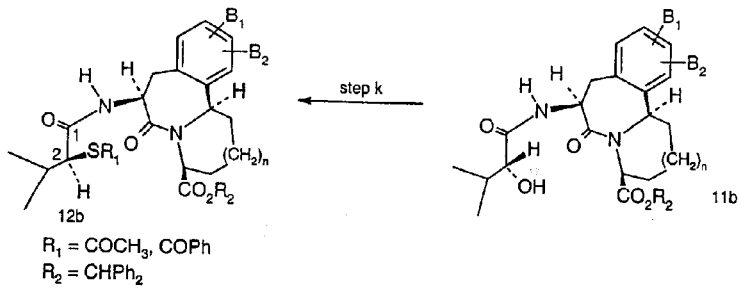

Column 13,
Line 49, "hydrocloric acid and saturated with" should read as -- hydrochloric acid and with saturated --

Column 14,
Line 2, reads as "hexane) on 200 ml silica using 20% ethyl acetate. The" and should read should read -- hexane) on 200 ml silica. The --
Line 17, the structure reads as:

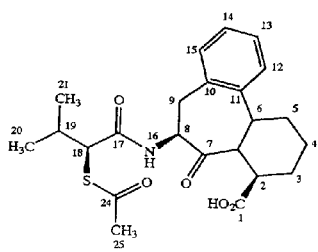

and should read as:

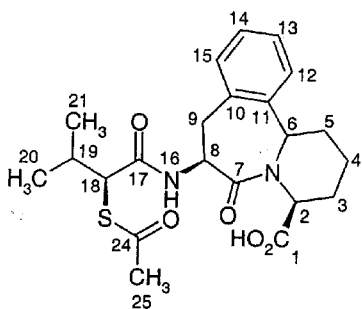

UNITED STATES PATENT AND TRADEMARK OFFICE
CERTIFICATE OF CORRECTION

PATENT NO.   : 6,602,866 B2
DATED         : August 5, 2003
INVENTOR(S)  : Flynn et al.

It is certified that error appears in the above-identified patent and that said Letters Patent is hereby corrected as shown below:

<u>Column 16,</u>
Line 63, reads as "agents such as alginic acid, Primojel®;, corn starch and the" should read as -- agents such as alginic acid, Primojel®, corn starch and the --

<u>Column 17,</u>
Line 13, reads as "non toxic in the amounts used." and should read as -- non-toxic in the amounts used. --

<u>Column 19,</u>
Line 10, reads as "methyl-1-oxobutyl]amino]-,2,3,4,5,6,7,8, 1b-octahydro-6-" and should read as -- methyl-1-oxobutyl]amino]-1,2,3,4,5,6,7,8, 12b-octahydro-6- --
Line 42, reads as "alkanoyl benzoyl, or an acyl group of the formula" and should read as -- alkanoyl, benzoyl, or an acyl group of the formula --

Signed and Sealed this

Seventeenth Day of February, 2004

JON W. DUDAS
*Acting Director of the United States Patent and Trademark Office*